United States Patent [19]
Stibrany et al.

[11] Patent Number: 5,183,945
[45] Date of Patent: Feb. 2, 1993

[54] CATALYTIC PRODUCTION OF ARYL ALKYL HYDROPEROXIDES BY MANGANESE COMPLEXES

[75] Inventors: Robert T. Stibrany, Long Valley; Sergiu M. Gorun, Upper Montclair, both of N.J.

[73] Assignee: Exxon Research and Engineering Company, Florham Park, N.J.

[21] Appl. No.: 794,096

[22] Filed: Nov. 18, 1991

[51] Int. Cl.$^5$ .................... C07C 409/22; C07C 409/00
[52] U.S. Cl. ...................................... 568/574; 568/573; 568/575; 568/577
[58] Field of Search ................ 568/573, 574, 575, 577

[56] References Cited

U.S. PATENT DOCUMENTS 2,954,405  9/1960  Hock et al. .................... 568/575
4,013,725  5/1977  Yonemitsa .................... 568/575

FOREIGN PATENT DOCUMENTS 150511  10/1978  U.S.S.R. .................... 568/575
745120  2/1956  United Kingdom .................... 568/574

Primary Examiner—Werren B. Lone
Attorney, Agent, or Firm—Joseph J. Dvorak; Linda M. Scuorzo

[57] ABSTRACT

This invention relates to a process for preparing organic hydroperoxides by selectively oxidizing aryl alkyl hydrocarbons to their corresponding organic hydroperoxides using a catalyst certain tetranuclear manganese complexes. The process is carried out without appreciable decomposition by the catalyst of the resulting organic hydroperoxides, and without oxidation by the catalyst of other hydrocarbons present in the starting mixture.

The process of the present invention is useful for producing organic hydroperoxides, which themselves are useful as starting materials for a number of commercial reactions, for example, phenol and acetone production.

9 Claims, 2 Drawing Sheets

CATALYTIC PRODUCTION OF ARYL ALKYL HYDROPEROXIDES BY MANGANESE COMPLEXES

BACKGROUND OF THE INVENTION

1. Field of the Invention

This invention relates to a process for preparing organic hydroperoxides by selectively converting aryl alkyl hydrocarbons in the presence of an oxygen-containing gas and certain tetranuclear manganese complexes as a catalyst. Such conversion is carried out without decomposition to any appreciable extent of the resulting organic hydroperoxides.

2. Description of the Prior Art

The production of organic hydroperoxides from aryl alkyl hydrocarbons in the presence of various transition metal salt complexes has been described in the literature (see, for example, U.S. Pat. No. 2,954,405 concerning the production of organic hydroperoxides by autooxidation of hydrocarbons in the presence of molecular oxygen and metal phthalocyanines as catalysts). In '405, certain phthalocyanines were found to catalyze autooxidation without significant decomposition of the organic hydroperoxides to undesirable side products, as was the case in many previous processes. However, U.S. Pat No. 2,954,405 is not the same catalyst complex. Further, when the '405 catalyst contains manganese, the reaction does, in fact, produce undesirable by-products. Therefore, it does not teach nor disclose the process of the present invention. Similarly, U.S. Pat. No. 4,013,725 discloses a process for preparing hydroperoxides in a homogeneous system by autooxidizing secondary alkyl group-substituted methylbenzenes in the presence of water, a base, an oxygen containing gas, and a water-soluble chelate compound in which multidentate ligands are coordinated to at least one metal from the class of cobalt, nickel, manganese, copper, and iron. The multidentate ligand may include nitrogen containing polycarboxylic acids. The process may be distinguished from that of the present invention on several grounds. First, while both the organic ligand used in the process of the '725 patent and the present invention are amino acids and, hence, contain both amino and carboxyl groups, the process of the present invention uses a catalyst that contains an additional essential alkoxide group, which is not taught nor disclosed in the process of the '725 patent. Second, the process of the '725 patent requires the presence of significant amounts of water to dissolve the catalyst and to carry out the hydroperoxidation process. The present invention adds the catalyst in situ: no water is required. Finally, the '725 patent requires continuous adjustment of the pH of the solution to a value between 5 and 7.5 using alkali salts. No additional reagents are required to adjust the pH in the process of the present invention.

In U.S. Pat. No. 5,025,101, applicants taught and claimed the tetranuclear manganese complexes and their method of preparation, which complexes are used as the catalyst in the process of the present invention. In '101, applicants found that the complexes were useful as hydrogen peroxide decomposers. Applicants have now discovered the unexpected result that these complexes are effective in the process of selectively producing organic hydroperoxides from aryl alkyl hydrocarbons, but that they do not catalyze the decomposition of those organic hydroperoxides. The result is unexpected since transition metal ions are generally known to decompose hydroperoxides catalytically; thus, the expectation is that a metal complex that vigorously decomposes them will also decompose organic hydroperoxides.

SUMMARY OF THE INVENTION

This invention relates to a process for preparing organic hydroperoxides comprising selectively oxidizing aryl alkyl hydrocarbons in situ to their corresponding organic hydroperoxides using as a catalyst certain tetranuclear manganese complexes. The process is carried out without decomposition of the resulting organic hydroperoxides to any appreciable extent.

The process of the present invention is useful for producing organic hydroperoxides, which themselves are useful as starting materials for a number of commercial reactions; for example, the production of phenol and acetone from cumene hydroperoxide (also referred to as cumyl hydroperoxide).

DETAILED DESCRIPTION OF THE INVENTION

Figure 1:
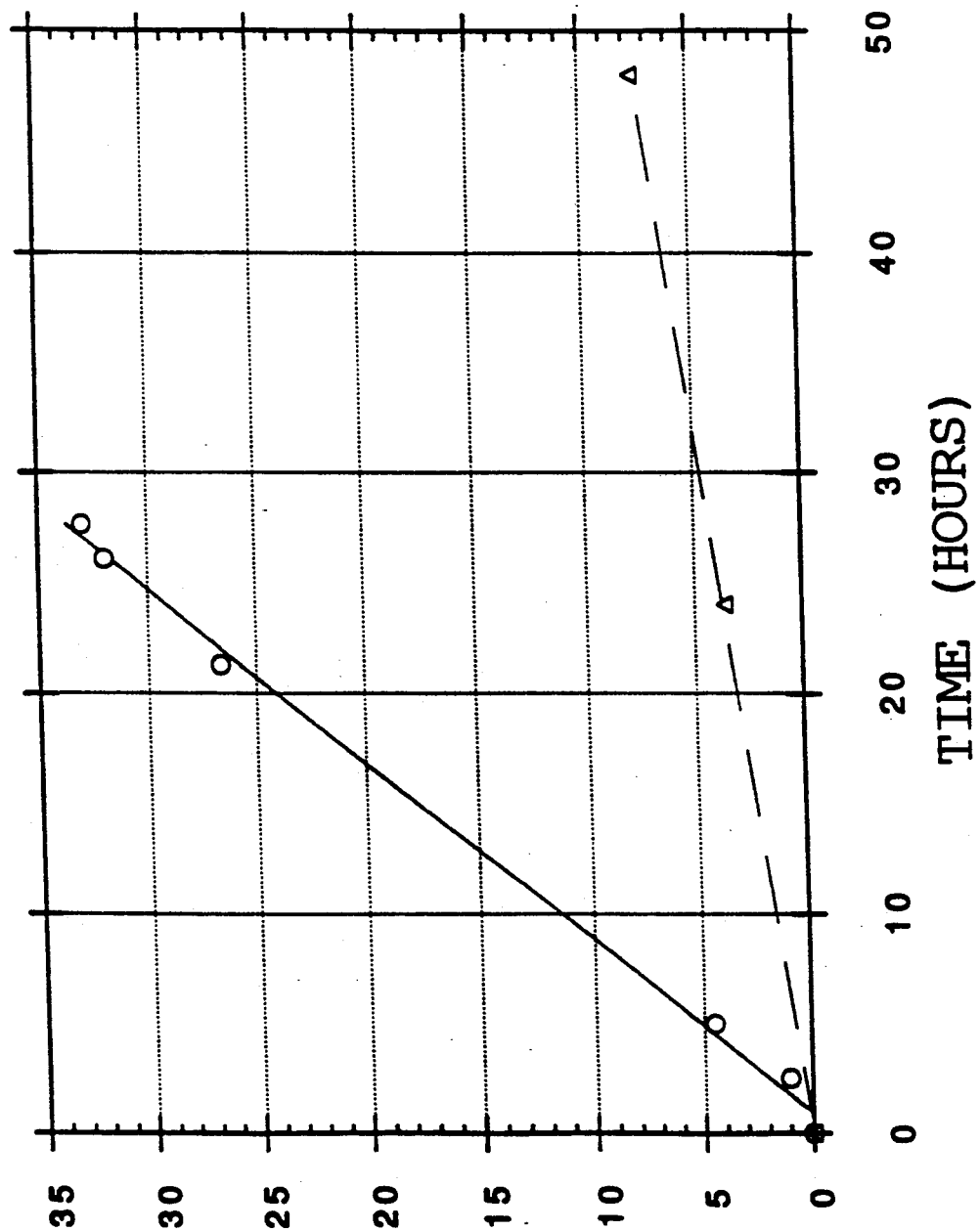
FIG. 1 shows the weight percent of cumene hydroperoxide produced from cumene in the presence of air and the catalyst by the process of the present invention contrasted with the amount of cumene hydroperoxide produced in the presence of cumene, air and cumene hydroperoxide as an initiator. The figure shows that the catalyzed process of the present invention increases the reaction rate by a factor of approximately 10 over the process that uses cumene hydroperoxide as an initiator.
Figure 2:
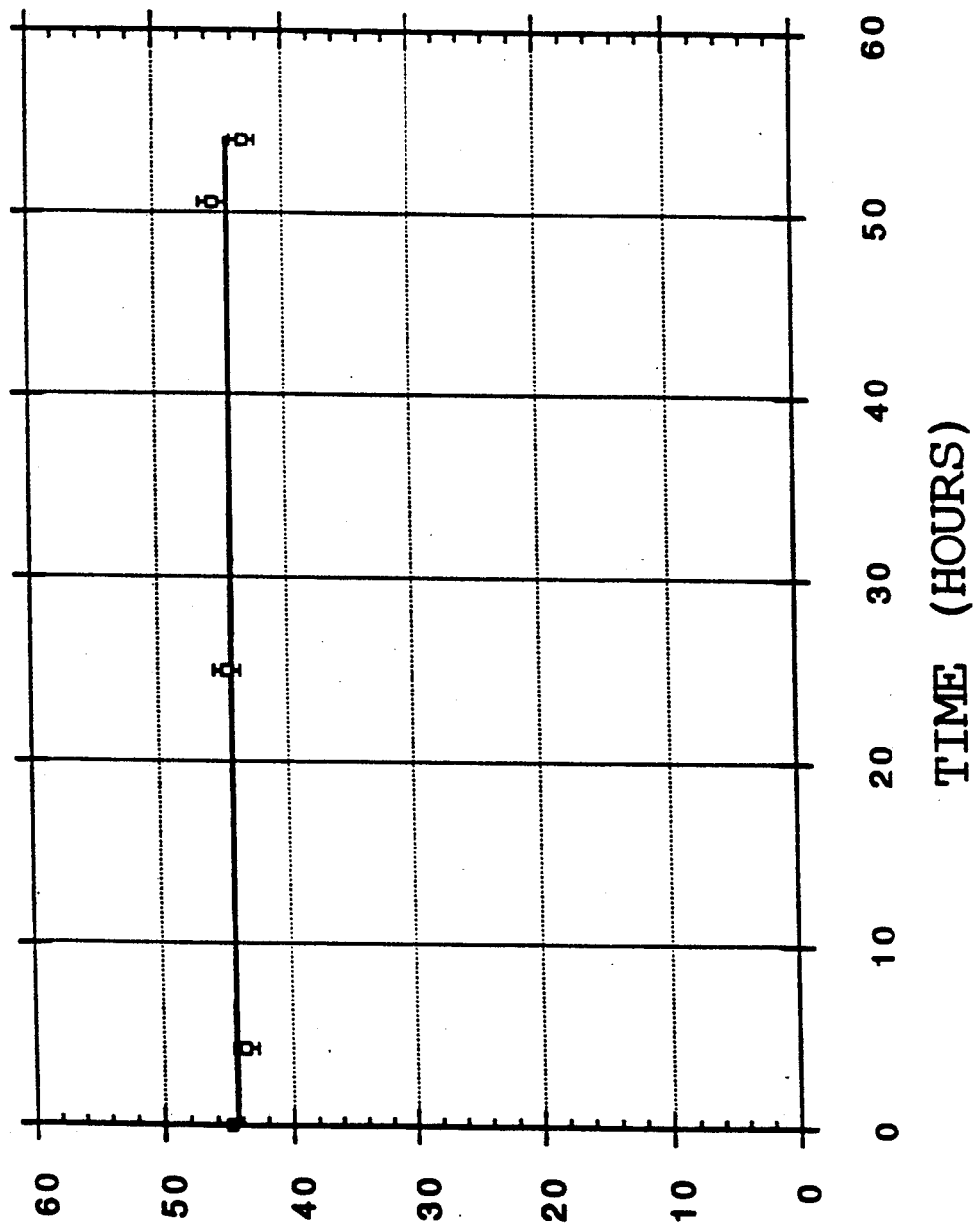
FIG. 2 shows the lack of cumene hydroperoxide degradation by the catalyst.

The process of the present invention is carried out in a heterogeneous system by contacting aryl alkyl hydrocarbons alone or a mixture of aryl alkyl hydrocarbons and other hydrocarbons that do not decompose or deactivate the catalyst, preferably aromatic hydrocarbons with an oxygen-containing gas and a tetranuclear manganese complex catalyst in catalytically-effective amounts. The oxygen containing gas is preferably air or oxygen, more preferably air. The catalyst is present in any form that renders the system heterogeneous, preferably in solid form.

The process of the present invention is useful for producing organic hydroperoxides, which themselves are useful as starting materials for a number of commercial reactions, particularly phenol and acetone production.

The tetranuclear manganese complexes used as catalysts in the process of this invention have the general formula:

$$M_2[Mn_4(O)(OH)(O_2CR)_2L_2]$$

wherein M is an alkali metal or an alkaline earth metal, preferably magnesium, calcium, strontium, barium, potassium, sodium, lithium, and mixtures thereof, more preferably barium. R is selected from the group consisting of hydrogen and a hydrocarbyl group and L is a ligand having the formula:

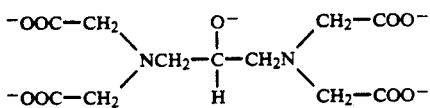

In the catalyst, when R is a hydrocarbyl group, preferably it will have from 1 to about 30 carbon atoms and, more preferably, is an alkyl group having from 1 to about 10 carbon atoms. When R is an aralkyl group, it preferably will have from 7 to about 10 carbon atoms. The catalyst's method of preparation is described in U.S. Pat. No. 5,025,101.

The catalyst in the process of the present invention is used in the solid state form obtained from the crystallization process described in U.S. Pat. No. 5,025,101. The aryl alkyl hydrocarbons employed as starting materials in this process may be obtained from commercial sources. The aryl alkyl hydrocarbons must have a melting point within the range of temperatures at which the process of the present invention is operated, or must be capable of being solubilized using an appropriate co-solvent that is inert to the process of the present invention. Further, the aryl alkyl hydrocarbons must contain a benzylic hydrogen, such that the hydrocarbon has the general formula:

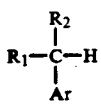

wherein $R_1$ and $R_2$ may be organo groups, preferably lower alkyl groups or hydrogen groups and may be the same or different and Ar is an aromatic.

The solvent for the reaction is preferably an excess amount of the starting hydrocarbon mixture.

The amount of catalyst used will vary depending upon the nature and amount of the organic starting material to be oxidized. In general from about 0.001 to about 0.5 parts by weight of catalyst per 100 parts of substrate and preferably from about 0.1 to about 0.2 parts per 100 parts of substrate are satisfactory.

Contacting is preferably by any means that achieves intimate contact, such as rapid bubbling or mechanic agitation. The flow rate of gas will vary depending on the reaction temperature and pressure, but should be sufficient to convert the aryl alkyl hydrocarbons to the corresponding organic hydroperoxides. In general there appears not to be an upper limit on the flowrate. In the case of cumene hydroperoxide preferably the flow rate should be up to about 10 liters/hr per 100 g. of cumene, preferably at least 2 liters/hr and in all cases sufficient to accomplish the reaction. The contacting is preferably carried out with air rather than oxygen, at at least 0.5 atm. pressure. It is within the skill of one ordinarily skilled in the art to select the appropriate pressure to effect the optimum reaction rate.

The reaction temperature may range from about 0° C. to about 90° C., preferably from about 60° C. to about 80° C. Temperatures at the lower end of the preferred range are more desirable.

It is an important aspect of the process of the present invention that it results in the selective oxygenation of the aryl alkyl hydrocarbons in the starting material in the presence of the tetranuclear manganese complex and an oxygen containing gas, but does not oxygenate to any appreciable extent (i.e., within the limits of experimental error) aromatic or aliphatic hydrocarbons present in the starting material. The process also does not require the presence of an initiator in the form of a small amount of the resulting organic hydroperoxide, as has been the case in other processes. The catalyzed process of the present invention increases the reaction rate by a factor of approximately 10 over the process that uses cumene hydroperoxide as an initiator.

It is also an important aspect of the present invention that while the tetranuclear manganese complex catalyzes the formation of organic hydroperoxides from the corresponding alkyl aromatic hydrocarbons it does not catalyze the decomposition of these organic hydroperoxides thus formed to any appreciable extent, i.e., within the limits of experimental error. For example, in the case of cumene hydroperoxide, no decomposition was found to occur at 65° C. within the limits of experimental error (about 1%) even when the cumene hydroperoxide remained in contact with the catalyst for a period of 100 hours. This ability to catalyze the formation of organic hydroperoxides without also catalyzing their decomposition is unexpected given the fact that the catalyst was previously found to be useful in catalyzing the decomposition of hydrogen peroxide ($H_2O_2$), and given the fact that certain manganese salts of various nuclearity and topology are well known to those ordinarily skilled in the art to decompose organic hydroperoxides.

The formation of the corresponding organic hydroperoxides can be monitored, for example, by analyzing aliquots by NMR, iodometric titration, chromatography or other means readily known to one skilled in the art. The organic hydroperoxides are readily recovered from the reaction mixture by conventional methods, for example distillation, and as a result, the process may be run in batch or continuously. In a continuous process, the aryl alkyl hydrocarbon starting material may be passed over a catalyst bed or otherwise contacted with the catalyst, the organic hydroperoxide withdrawn and the organic starting material recycled. When run in batch, the amount of starting material converted to organic hydroperoxide will depend on the time at which the reaction is stopped.

EXAMPLE 1

0.1 g of solid barium tetranuclear manganese catalyst was added to 50 g of neat cumene in a flask. Air was bubbled through the reaction mixture at a rate of 30 ml/min. The reaction was run at 65° C., 1 atm. pressure. After 30 hours, the reaction was stopped. Analysis of the sample by titration showed approximately 40% of the cumene was converted to cumene hydroperoxide. The rate of conversion per hour was approximately 1.3% per hour.

Table 1 shows the hydroperoxidation rates of certain aryl alkyl benzenes. The reactions were run under conditions specified in Example 1.

TABLE 1

| Alkyl Benzene | Hydroperoxidation Rate (Wt % per hour) |
|---|---|
| isopropyl (cumene) | 1.3 |
| ethyl | 0.2 |
| sec-butyl | 0.18 |
| n-butyl | 0.1 |
| n-propyl | 0.1 |
| dimethyl (xylene) | 0.01 |

EXAMPLE 2

0.1 g of solid barium tetranuclear manganese catalyst was added to 50 g of 40 wt. % cumene hydroperoxide in cumene. The reaction was run at 65° C., 1 atm. and samples were taken at from 0 to 100 hours. Samples were analyzed by titration for the loss of cumene hydroperoxide. Within the limits of experimental error (approximately 1%), no decomposition of the cumene hydroperoxide was observed.

What is claimed is:

1. A process for preparing organic hydroperoxides by selectively converting aryl alkyl hydrocarbons to the corresponding organic hydroperoxides, comprising: contacting aryl alkyl hydrocarbons wherein the aryl alkyl hydrocarbons contain a benzylic hydrogen of the general formula:

$$R_1-\underset{\underset{Ar}{|}}{\overset{\overset{R_2}{|}}{C}}-H$$

wherein $R_1$ and $R_2$ may be organo groups or hydrogen groups and may be the same or different from each other with an oxygen-containing gas and a catalytically effective amount of a tetranuclear manganese complex catalyst having the formula:

$$M_2[Mn_4(O)(OH)(O_2CR)_2L_2]$$

wherein M is an alkali metal or an alkaline earth metal, R is selected from the group consisting of hydrogen and a hydrocarbyl group and L is a ligand having the formula:

$$\begin{array}{c}^{-}OOC-CH_2\\ ^{-}OOC-CH_2\end{array}NCH_2-\underset{\underset{H}{|}}{\overset{\overset{O^-}{|}}{C}}-CH_2N\begin{array}{c}CH_2-COO^-\\ CH_2-COO^-\end{array}$$

to produce the corresponding organic hydroperoxides.

2. The process of claim 1 wherein M is magnesium, calcium, strontium, potassium, sodium, lithium, barium and mixtures thereof.

3. The process of claim 2 wherein M is barium.

4. The process as in claim 1 wherein the R group of the tetranuclear manganese complex catalyst is a hydrocarbyl group selected from the group consisting of alkyl groups having from 1 to about 30 carbon atoms and aryl alkyl groups.

5. The process of claim 1 wherein the aryl alkyl hydrocarbon is cumene.

6. The process as in claim 1 wherein the organic hydroperoxides are not decomposed by the catalyst to any appreciable extent.

7. The process of claim 1 wherein the aryl alkyl hydrocarbons are liquid at operating temperatures and pressures.

8. The process of claim 1 wherein the aryl alkyl hydrocarbon is soluble in an inert cosolvent.

9. A process for preparing organic hydroperoxides from a mixture of hydrocarbons, comprising selectively converting aryl alkyl hydrocarbons, wherein the aryl alkyl hydrocarbons contain a benzylic hydrogen of the general formula:

$$R_1-\underset{\underset{Ar}{|}}{\overset{\overset{R_2}{|}}{C}}-H$$

wherein $R_1$ and $R_2$ may be organo groups or hydrogen groups and may be the same or different from each other, in a mixture of hydrocarbons by contacting said hydrocarbons with an oxygen-containing gas and a catalytically effective amount of a tetranuclear manganese complex catalyst having the formula:

$$M_2[Mn_4(O)(OH)(O_2CR)_2L_2]$$

wherein M is an alkali metal or an alkaline earth metal, R is selected from the group consisting of hydrogen and a hydrocarbyl group and L is a ligand having the formula:

$$\begin{array}{c}^{-}OOC-CH_2\\ ^{-}OOC-CH_2\end{array}NCH_2-\underset{\underset{H}{|}}{\overset{\overset{O^-}{|}}{C}}-CH_2N\begin{array}{c}CH_2-COO^-\\ CH_2-COO^-\end{array}$$

to produce the corresponding organic hydroperoxides.

* * * * *